(12) United States Patent
Steinhardt et al.

(10) Patent No.: US 10,888,418 B2
(45) Date of Patent: Jan. 12, 2021

(54) PASSIVE MIDDLE EAR PROSTHESIS (71) Applicant: MED-EL Elektromedizinische Geraete GmbH, Innsbruck (AT)

(72) Inventors: Uwe Steinhardt, Hirrlingen (DE); Clemens Kuen, Imst (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 16/327,883

(22) PCT Filed: Sep. 12, 2017

(86) PCT No.: PCT/US2017/051047
§ 371 (c)(1),
(2) Date: Feb. 25, 2019

(87) PCT Pub. No.: WO2018/052866
PCT Pub. Date: Mar. 22, 2018

(65) Prior Publication Data
US 2019/0201189 A1    Jul. 4, 2019

Related U.S. Application Data

(60) Provisional application No. 62/393,696, filed on Sep. 13, 2016.

(51) Int. Cl.
*A61F 2/18* (2006.01)
*A61L 27/04* (2006.01)

(52) U.S. Cl.
CPC ............... *A61F 2/18* (2013.01); *A61L 27/04* (2013.01); *A61F 2002/183* (2013.01);
(Continued)

(58) Field of Classification Search
CPC .... A61F 2/18; A61F 11/004; A61F 2002/183; A61F 2220/0008; A61F 2230/0013;
(Continued)

(56) References Cited

U.S. PATENT DOCUMENTS

2002/0045939 A1   4/2002   Kurz
2007/0255405 A1*  11/2007  Reitan ................... A61F 2/18
                                                       623/10
(Continued)

FOREIGN PATENT DOCUMENTS

CN    101461743 A    6/2009
CN    101889909 A    11/2010
(Continued)

OTHER PUBLICATIONS

International Searching Authority/U.S. International Search Report and Written Opinion, Application No. PCT/US2017/051047, dated Nov. 20, 2017, 26 pages.
(Continued)

*Primary Examiner* — Suba Ganesan
*Assistant Examiner* — Aren Patel
(74) *Attorney, Agent, or Firm* — Sunstein LLP (57) ABSTRACT

A middle ear prosthesis is made of a stiff deformable material and includes a planar head end with a central portion having a central diameter. The head end is adapted for engagement with a tympanic membrane from the middle ear of an implanted patient. An opposing pair of U-shaped stapes engagement legs bend down from the central portion so that an end distance between ends of the engagement legs is less than the central diameter. The engagement legs are adapted for adjustable length engagement with the stapes in the middle ear of the implanted patient. The head end and the engagement legs are adapted to transmit vibrations from the tympanic membrane to the stapes for perception as sound by the implanted patient.

17 Claims, 9 Drawing Sheets

(52) U.S. Cl.
CPC ........... *A61F 2220/0008* (2013.01); *A61F 2230/0013* (2013.01); *A61F 2230/0095* (2013.01); *A61F 2240/001* (2013.01); *A61L 2430/14* (2013.01)

(58) Field of Classification Search
CPC ....... A61F 2230/0095; A61F 2240/001; A61L 27/04; A61L 2430/14
USPC .......................................................... 623/10
See application file for complete search history.

(56) References Cited

U.S. PATENT DOCUMENTS

| | | | |
|---|---|---|---|
| 2008/0234817 A1* | 9/2008 | Huettenbrink | A61F 2/18 623/10 |
| 2009/0164010 A1 | 6/2009 | Steinhardt et al. | |
| 2009/0240332 A1 | 9/2009 | Steinhardt et al. | |
| 2010/0262236 A1 | 10/2010 | Steinhardt et al. | |
| 2010/0272299 A1* | 10/2010 | Van Schuylenbergh | H04R 25/606 381/315 |
| 2010/0317914 A1 | 12/2010 | Puria et al. | |
| 2011/0178364 A1 | 7/2011 | Ball et al. | |
| 2014/0094910 A1 | 4/2014 | Steinhardt et al. | |
| 2014/0343674 A1 | 11/2014 | Beoni | |
| 2016/0175093 A1* | 6/2016 | Babu | A61F 2/18 623/10 |

FOREIGN PATENT DOCUMENTS

| | | |
|---|---|---|
| DE | 19744789 A1 | 4/1998 |
| DE | 20014659 U1 | 11/2000 |
| DE | 10 2013 106 574 A1 | 12/2014 |
| EP | 2601909 A1 | 6/2013 |
| WO | WO 98/16175 | 4/1998 |
| WO | WO 2016/077411 A1 | 5/2016 |

OTHER PUBLICATIONS

China National Intellectual Property Administration, Search Report, Application No. 201780055268.7, dated Apr. 13, 2020, 4 pages.

* cited by examiner

PASSIVE MIDDLE EAR PROSTHESIS

This application is a 371 national phase entry of Patent Cooperation Treaty Application PCT/US2017/051047, filed Sep. 12, 2017, which in turn claims priority from U.S. Provisional Patent Application 62/393,696, filed Sep. 13, 2016, both of which are incorporated herein by reference in their entireties.

FIELD OF THE INVENTION

The present invention relates to medical implants, and more specifically to a novel ossicular prosthesis arrangement.

BACKGROUND ART

Figure 1:
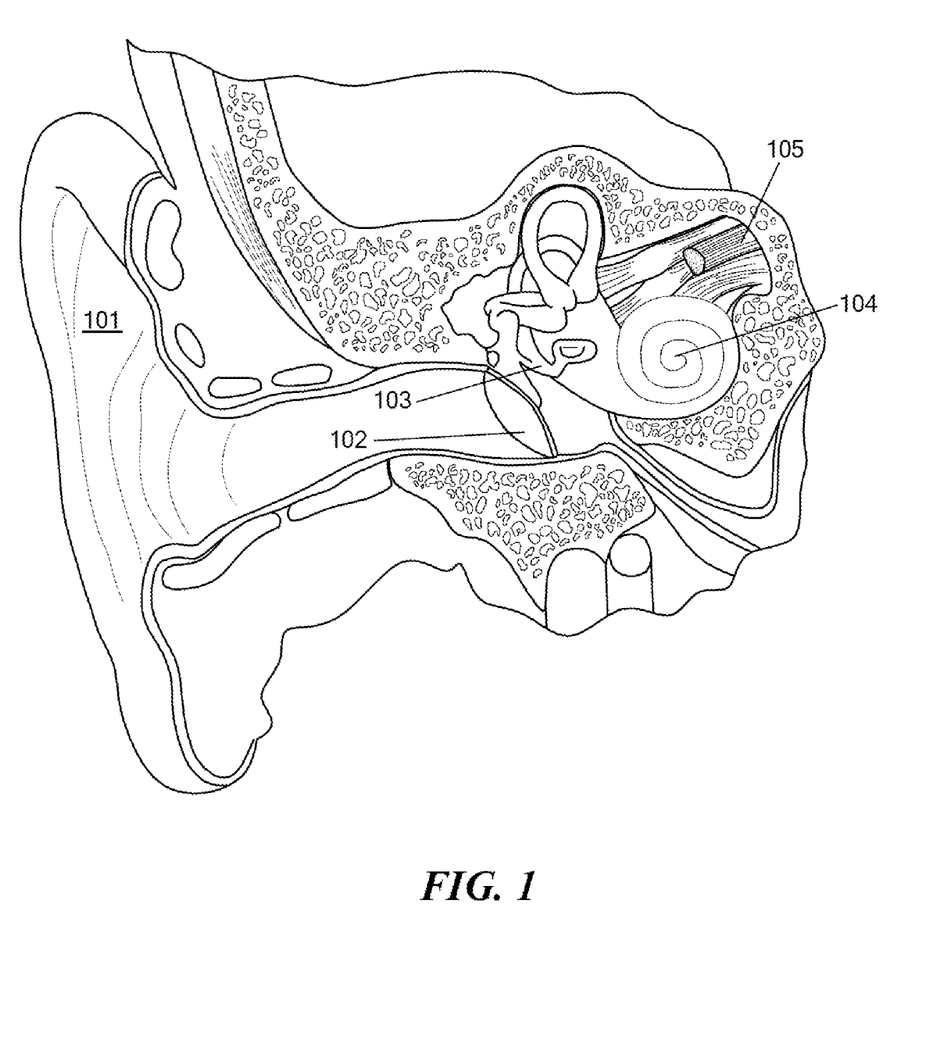
FIG. 1 shows various anatomical structures of a normal human ear.

A normal ear transmits sounds as shown in FIG. 1 through the outer ear 101 to the tympanic membrane (eardrum) 102, which moves the ossicles of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 105 reside. In response to received sounds transmitted by the middle ear 103, the fluid-filled cochlea 104 functions as a transducer to generate electric pulses which are transmitted to the cochlear nerve 105, and ultimately to the brain.

Figure 2:
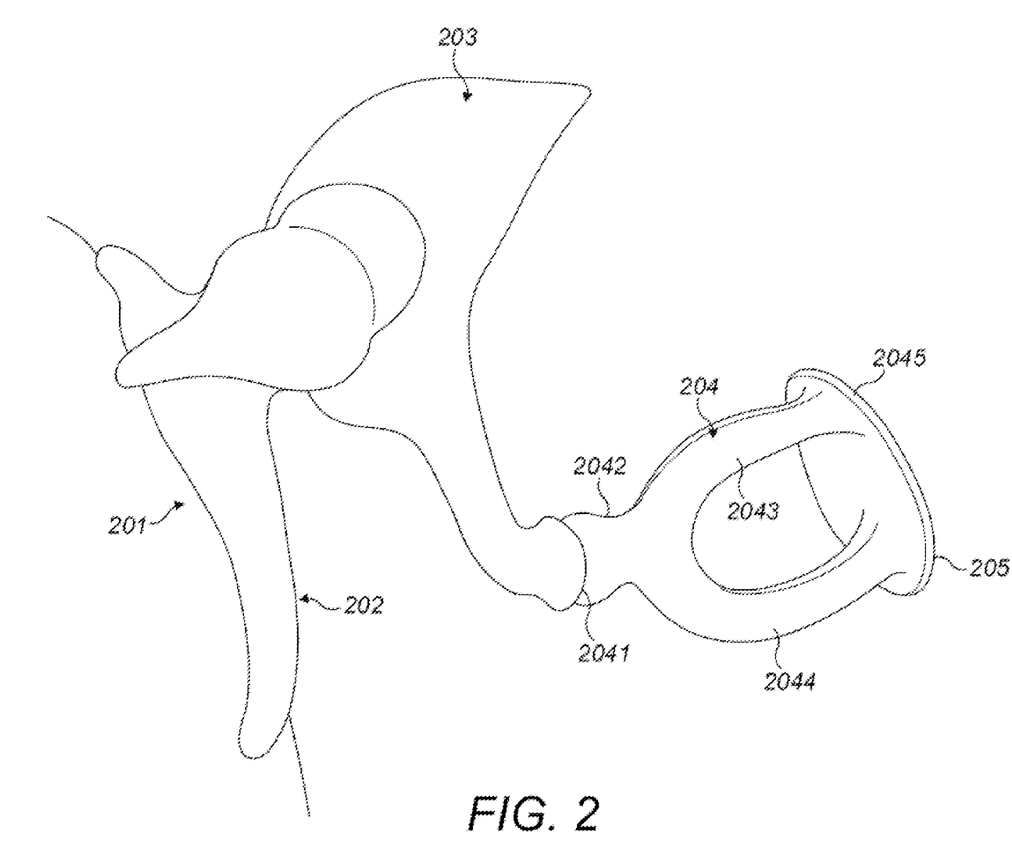
FIG. 2 shows details of the anatomy of the ossicles in the middle ear.

FIG. 2 shows the ossicles of the middle ear in greater anatomical detail where the malleus 202 ("hammer") is attached to the inside of the tympanic membrane 201. The outer ear funnels sound in to the tympanic membrane 201 causing it to vibrate. That vibration is felt by the malleus 202 which conducts it through the incus 203 to the stapes 204, in the process amplifying the vibrations over 20 times. The stapes 204 connects to the incus 203 at a stapes head 2041 at the end of the stapes neck 2042. The sound vibrations pass through the anterior crus 2043 and posterior crus 2044 to the stapes foot plate 2045. The stapes foot plate 2045 engages the oval window membrane 205 which transmits the vibrations into the fluid-filled interior of the cochlea for perception as sound.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Middle ear implants also have been developed that employ electromagnetic transducers to mechanically stimulate the structures of the middle ear 103.

In addition to such active hearing devices, there also are passive middle ear implants, which are structures that replace some or all of the ossicular chain to perform the required sound transmission and amplification to deliver the sound vibrations of the tympanic membrane across the oval window membrane into the cochlea. U.S. Pat. No. 8,936,637 (incorporated herein by reference in its entirety) shows a middle ear prosthesis with a U-shaped attaching mechanism with attachment legs 24' and 24". Similarly, U.S. Pat. No. 8,518,112 also has such attachment legs 21 and 21". WO 98/16175 (incorporated herein by reference in its entirety) describes a passive middle ear prosthesis with a bell shaped attachment clip 1'.

SUMMARY OF THE INVENTION

Embodiments of the present invention are directed to a middle ear prosthesis is made of a stiff deformable material (e.g., thin metal) and includes a planar head end with a central portion having a central diameter. The head end is adapted for engagement with a tympanic membrane from the middle ear of an implanted patient. An opposing pair of U-shaped stapes engagement legs bend down from the central portion so that an end distance between ends of the engagement legs is less than the central diameter. The engagement legs are adapted for adjustable length engagement with the stapes in the middle ear of the implanted patient. The head end and the engagement legs are adapted to transmit vibrations from the tympanic membrane to the stapes for perception as sound by the implanted patient.

The central portion may be thicker than other portions of the prosthesis and/or the engagement legs may be thinner than other portions of the prosthesis. The engagement legs may have a straight shape or a zig-zag shape. The u-shape of the engagement legs may have an opening that is either smaller or larger than the thickness of a portion of the stapes where engaged by the engagement legs. The engagement legs also may include leg end connectors at a distal end of each engagement leg that are adapted to connect corresponding ends of the opposing pair of engagement legs.

Specific embodiments may include a head end with opposing wings connected to and extending from the central portion. The opposing wings may include deformable wing extensions adapted for fixation of the head end at the tympanic membrane. And the wing extensions include extension end connectors that are adapted to connect opposing extension ends.

Embodiments of the present invention also include a method of forming a middle ear prosthesis that includes providing a planar sheet of stiff deformable material having a central portion connected to an opposing pair of U-shaped stapes engagement legs. The stapes engagement legs are then bent down from the planar sheet towards each other so that an end distance between ends of the engagement legs is less than the central diameter so as to adapt the engagement legs for engagement with the stapes of an implanted patient, and to leave a remaining portion of the planar sheet to form a head end adapted for engagement with the tympanic membrane from the middle ear of an implanted patient.

In further specific embodiments, the material may be thin metal material. Providing the planar sheet may include using micro-laser cutting to shape the planar sheet. The planar sheet may be less than 0.2 mm thick. The planar sheet may have a uniform thickness, or a non-uniform thickness. Bending the stapes engagement legs down from the planar sheet towards each other may place leg ends of the opposing pair of engagement legs closer to each other than a distance across the central portion where connected to the opposing pair of engagement legs.

DETAILED DESCRIPTION OF SPECIFIC EMBODIMENTS

Embodiments of the present invention are directed to a passive middle ear prosthesis (MEP) and corresponding method of producing such a MEP, which replaces a portion of the ossicular chain in the middle ear (at least the incus) and is placed between the tympanic membrane and at least a portion of the stapes. The dimensions of the middle ear may vary from patient to patient, so the MEP has a length adaptation mechanism to provide for adjustable length engagement with the stapes.

Figure 3A:
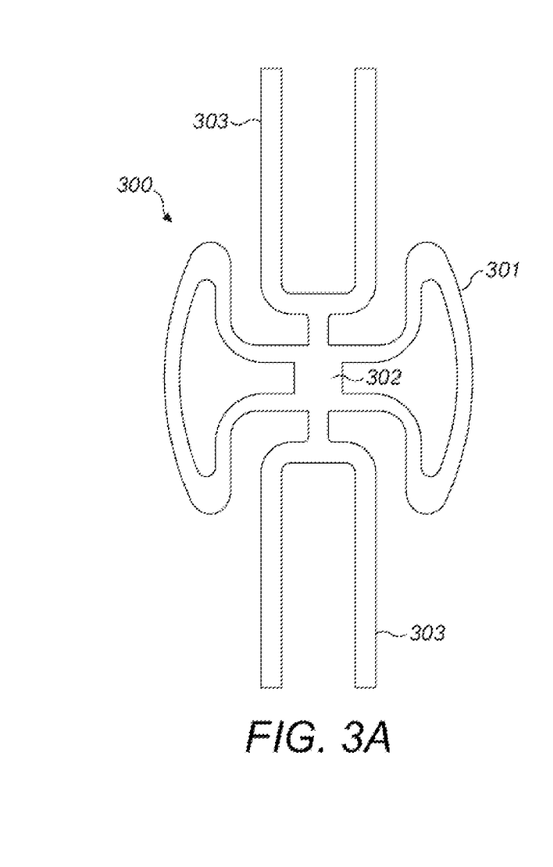
FIGS. 3A-3E show various views of a passive middle ear prosthesis according to an embodiment of the present invention.

FIGS. 3A-3E show various views of a passive middle ear prosthesis (MEP) 300 according to an embodiment of the present invention. The MEP 300 is formed by initially providing a planar sheet of stiff deformable material as shown in FIG. 3A with a central portion 302 connected to an opposing pair of U-shaped stapes engagement legs 303. In each such pair, the engagement legs 303 are substantially parallel to each other. A head end 301 of the MEP 300 extends out from the central portion 302 including a pair of opposing head wings. The specific forms of different embodiments of the initial planar sheet for the MEP 300 can be achieved by various known techniques such as by etching, micro-laser cutting, perforating, mechanical cutting, etc.

Given the application as a middle ear prosthesis, the thickness of the initial planar sheet as shown in FIG. 3A should be less than 0.2 mm, for example, between 0.15 mm and 0.1 mm. A thinner material results in a more flexible MEP 300, and consequently, the less risk of trauma to tissue in the middle ear, especially from the ends of the engagement legs 303 (see below). In some specific embodiments, the material may have a uniform thickness, while in other specific embodiments, the material may have a non-uniform thickness; for example, the central portion 302 may be thicker than other portions of the MEP 300 and/or the engagement legs 303 may be thinner than other portions of the MEP 300.

Figure 3B:
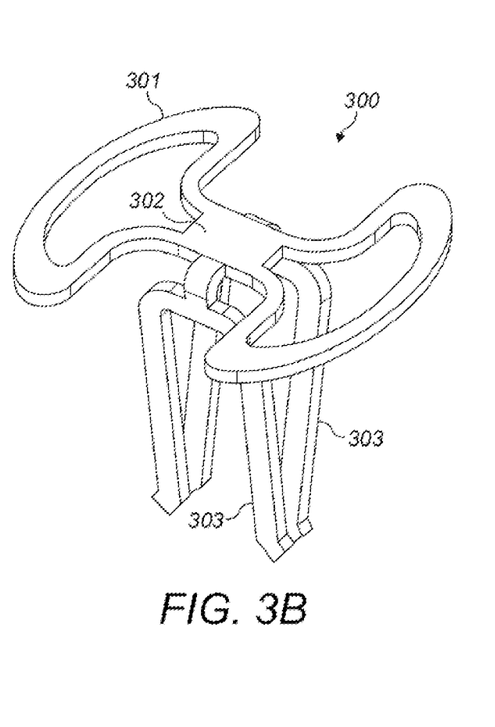
Figure 3C:
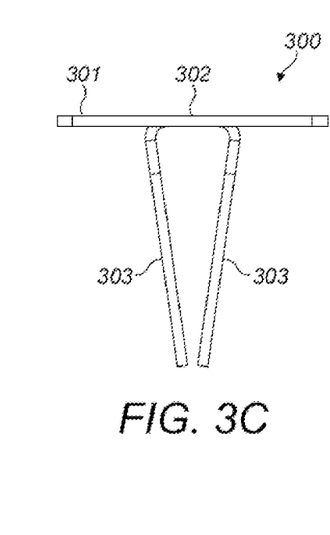

The stapes engagement legs 303 are then bent down from the planar sheet towards each other, as shown in FIG. 3B, so that an end distance between ends of the engagement legs 303 is less than the central diameter of the central portion 302, as shown in FIG. 3C, so as to adapt the engagement legs 303 for adjustable length engagement with the stapes of an implanted patient (as explained below). After bending, the remaining portion of the planar sheet forms a head end 301 with the central portion 302 that is adapted for engagement with the tympanic membrane from the middle ear of an implanted patient. The head end 301 and the engagement legs 303 are adapted to transmit vibrations from the tympanic membrane to the stapes for perception as sound by the implanted patient.

Figure 3D:
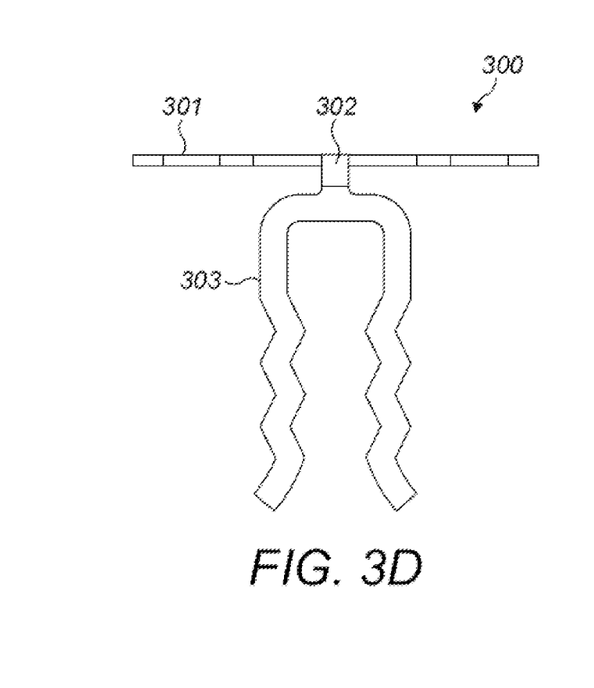
Figure 3E:
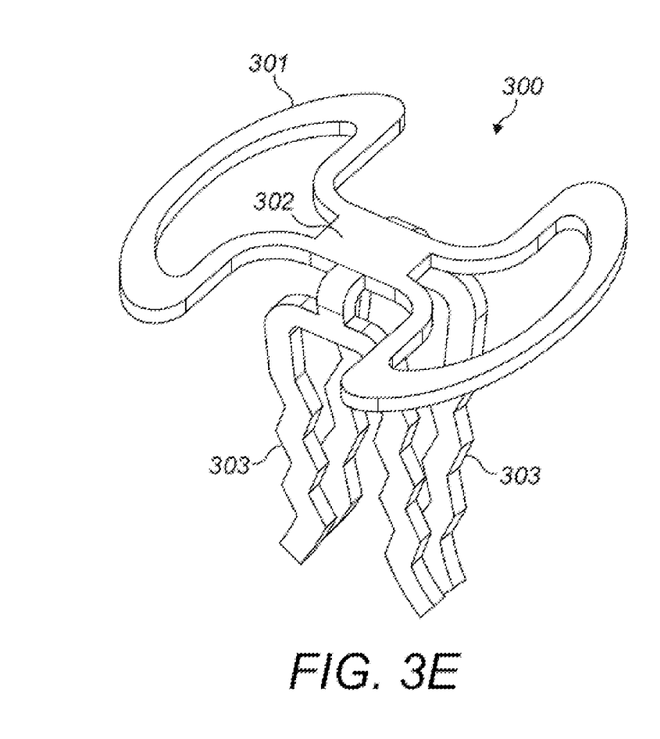

In the specific embodiment shown in FIGS. 3A-3C, the engagement legs 303 have a straight shape. FIGS. 3D-3E show an alternative embodiment where the engagement legs 303 have a zig-zag shape. Each U-shaped pair of engagement legs 303 is flat and may be adjusted/oriented independently of the other pair.

The U-shape of the engagement legs 303 may have an opening that is either a bit smaller or a bit larger than the thickness of the stapes where it is engaged by the legs. The MEP 300 is designed such that the distance between each of the engagement legs 300 in a given U-shaped pair is comparable to the thickness of the portion of the stapes over which the engagement legs 303 are moved—i.e., the stapes neck 2042 and possibly the anterior and posterior crus. When this distance between paired engagement legs 303 is slightly smaller than thickness of the stapes 204 over which they pass, the U-shape and the thinness of the engagement legs 303 provides some flexibility such that a bias load after insertion of the MEP 300 can translate into a widening of the U shape, thus reducing the bias load onto the stapes foot plate and, consequently, onto the oval window membrane. In the alternative case when distance between the engagement legs 303 of a given pair is slightly larger than the dimension of the engaged portions of the stapes 204, it surprisingly turns out that the MEP 300 still can be attached sufficiently to the stapes 204 because the viscous environment (body fluids) surrounding the stapes 204 provides sufficient adhesion force between MEP 300 and stapes tissue to maintain the MEP 300 in place. Then sometime after implantation, tissue grows over the implanted MEP 300 further securing it in place.

Existing middle ear prostheses for a comparable purpose (e.g., prostheses from the TTP-VARIC or TTP-VARIO system of Heinz Kurz GmbH Medizintechnik) are provided in form of a set of multiple prostheses each having different lengths. The surgeon has to use a sizer to assess the required length for the prosthesis for a given specific patient. If the surgeon for whatever reason doesn't choose the best prosthesis out of the set, there can be a bias load on the stapes foot plate after implantation because the length of the middle ear chain of ear drum-prosthesis-stapes does not adequately match the natural distance between ear drum and stapes. Such a bias load on the stapes foot plate can traumatize the membrane of the oval window leading to a permanent loss of flexibility and, consequently, to some further degree of conductive hearing loss.

Figure 4A:
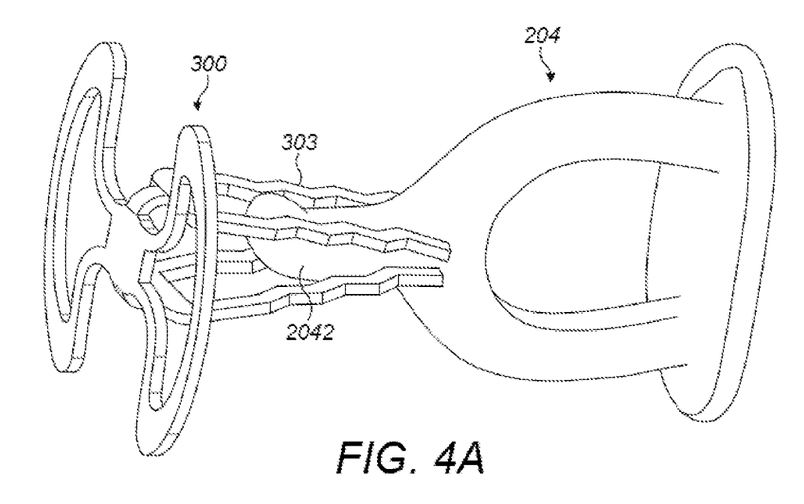
FIGS. 4A-4B show how a middle ear prosthesis according to an embodiment of the present invention engages the stapes in an implanted patient.
Figure 4B:
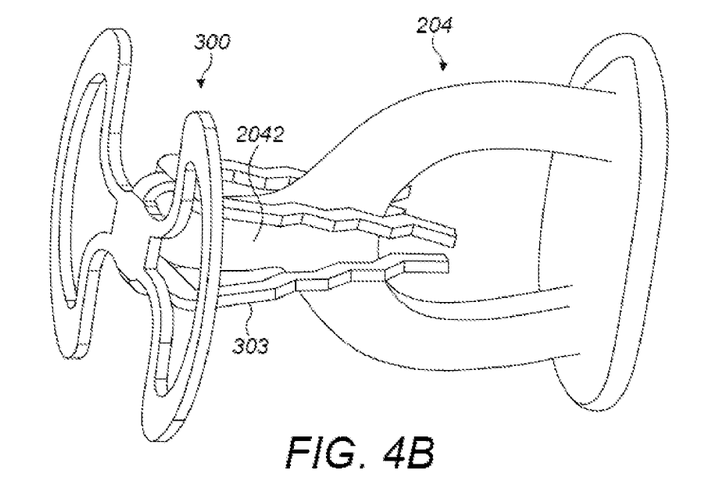

By contrast, the relatively long engagement legs 303 as used in embodiments of the present invention advantageously provides a means of intra-operative length adjustment to accommodate the varying distances between the tympanic membrane and the oval window membrane in different specific patients. As shown in FIG. 4A, the MEP 300 can be partially fit over the neck 2042 of stapes 204 to provide for a relatively large distance between the tympanic membrane and the oval window membrane. FIG. 4B shows a case where the MEP 300 fits more deeply over the stapes 204 to accommodate a relatively short distance between the tympanic membrane and the oval window membrane.

Figure 5:
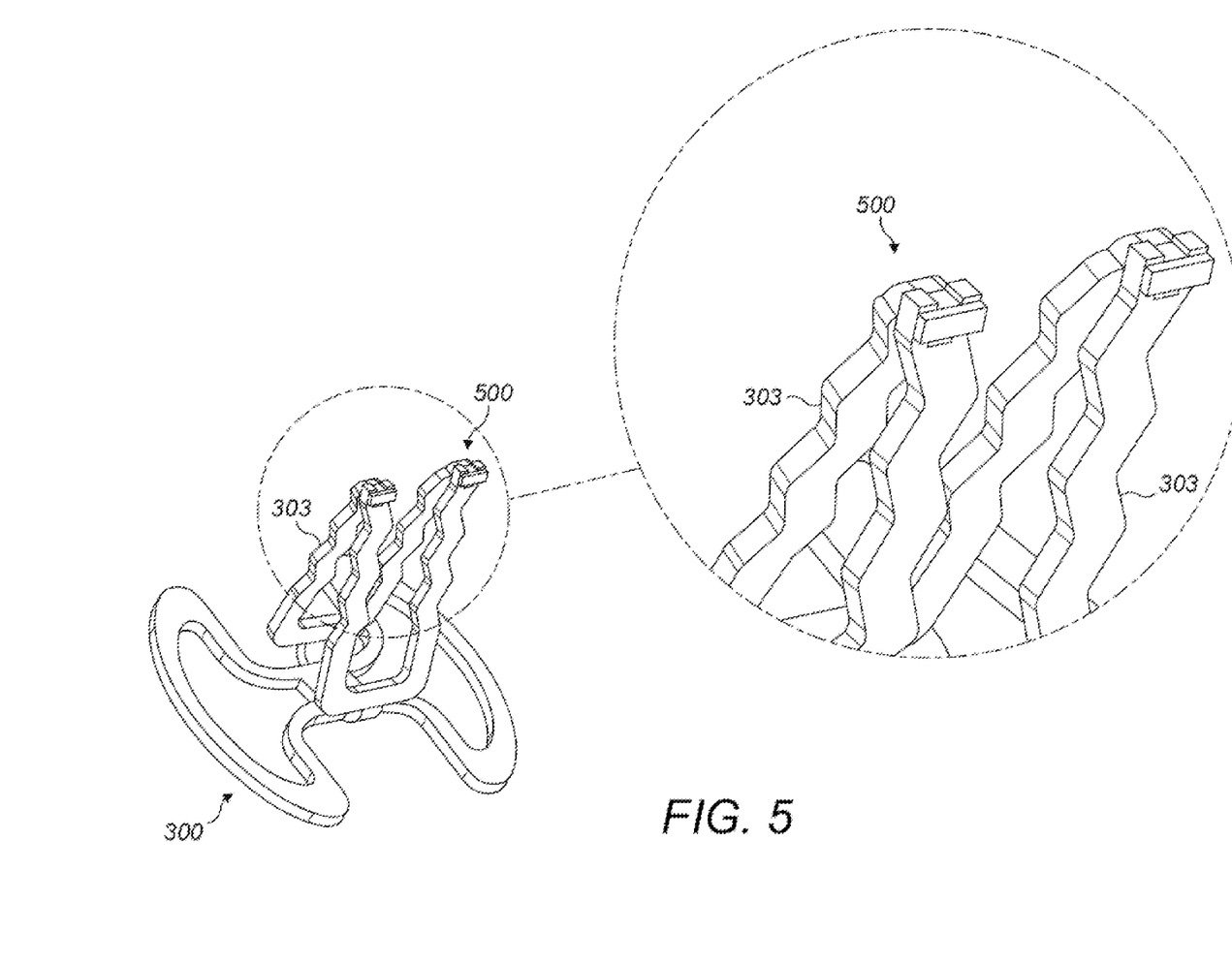
FIG. 5 shows structural details of leg end connectors according to an embodiment of the present invention.

After moving the MEP 300 into its desired position, the engagement legs 303 also may be slightly compressed at or near their open ends by use of an appropriate surgical instrument in order to further fixate them in their position. For such functionality, it may be useful for the engagement legs 303 to have a zig-zag shape (as shown in FIGS. 3D-3E) to facilitate the fixation of the engagement legs 303 at the stapes 204 (e.g., at the posterior and anterior crus of the stapes 204). A typical distance between two adjacent maximum points of the zig-zag shape usefully may be, for example, 0.5 mm, and between maximum and minimum points of the zig-zag shape, 0.4 mm. As shown in FIG. 5, the engagement legs 303 also may include leg end connectors 500 at a distal end of each engagement leg 303 that are adapted to connect corresponding ends of the opposing pair of engagement legs 303.

Figure 6A:
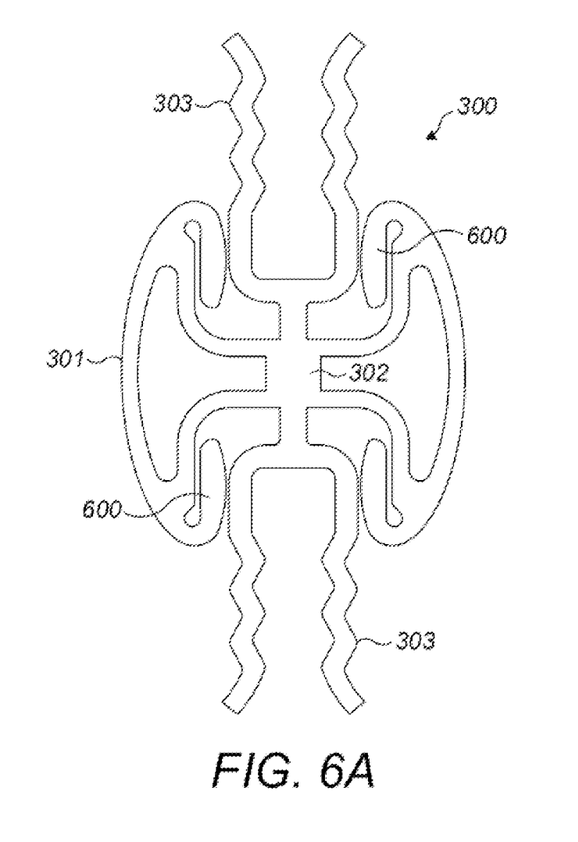
FIGS. 6A-6B show an embodiment of a middle ear prosthesis with wing extensions on the head end.
Figure 6B:
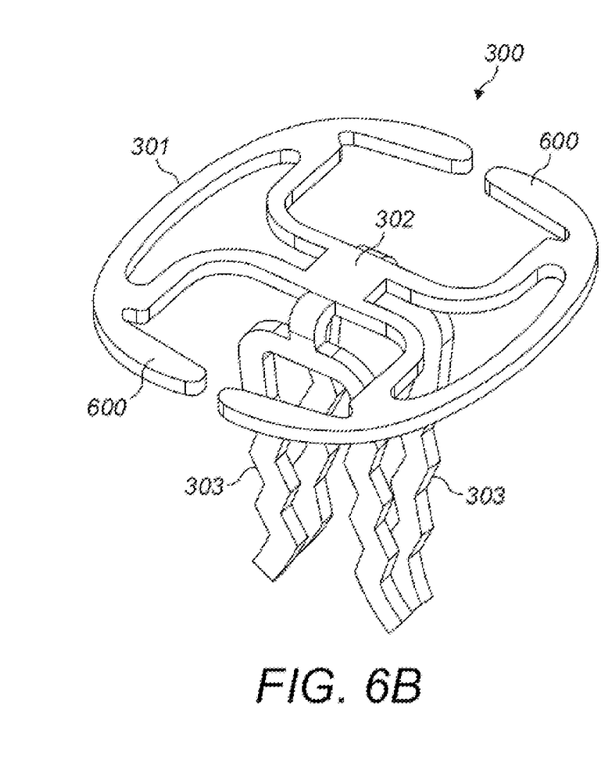
Figure 7:
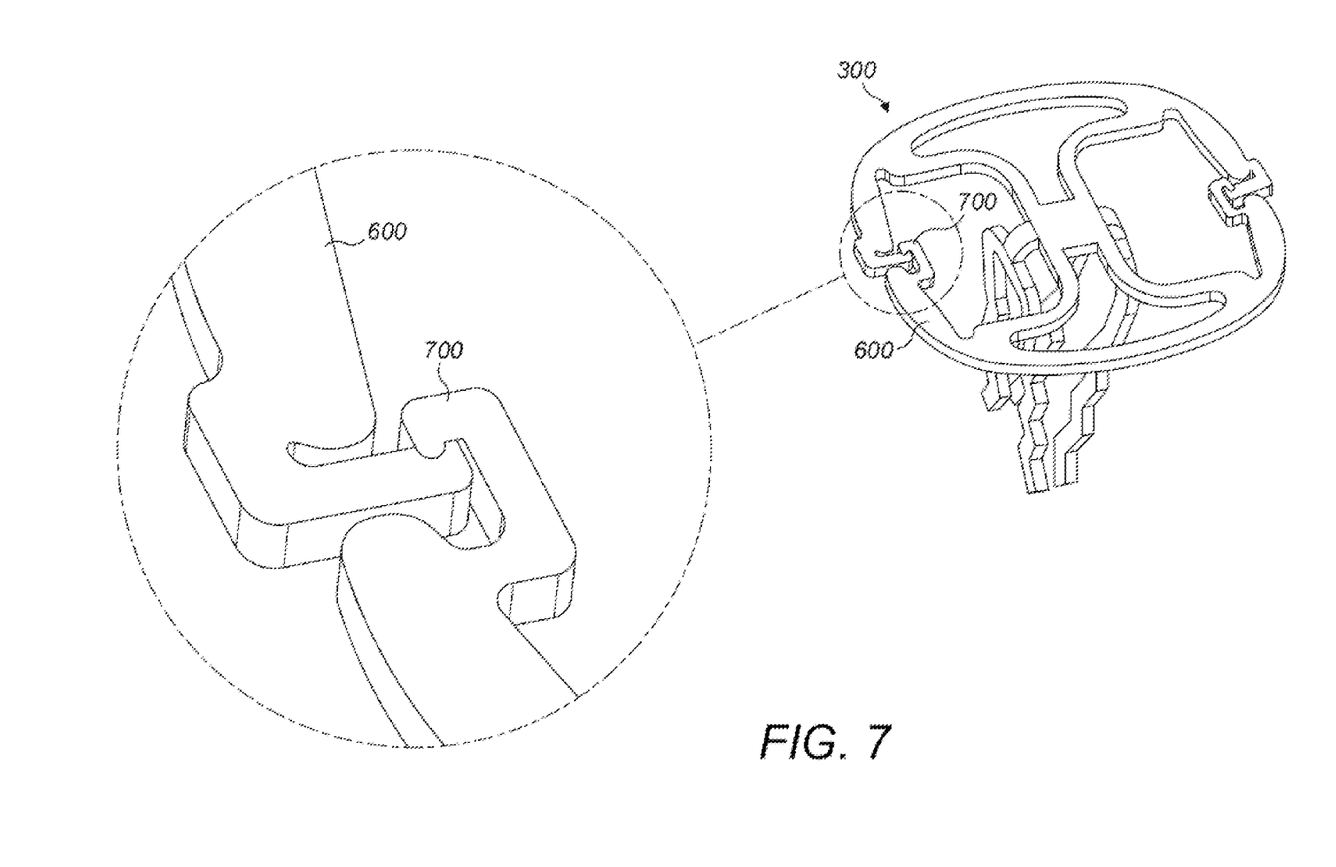
FIG. 7 shows an embodiment with wing extension connectors.
Figure 8A:
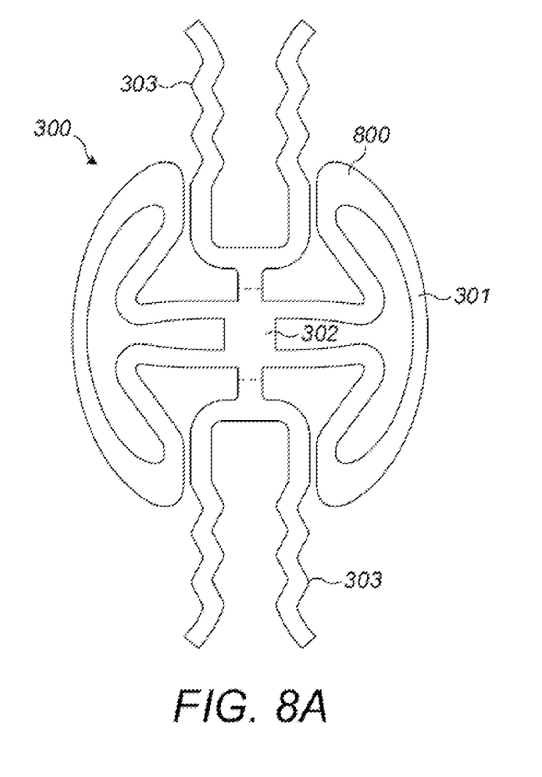
FIGS. 8A-8B show an embodiment with extended deformable wings.
Figure 8B:
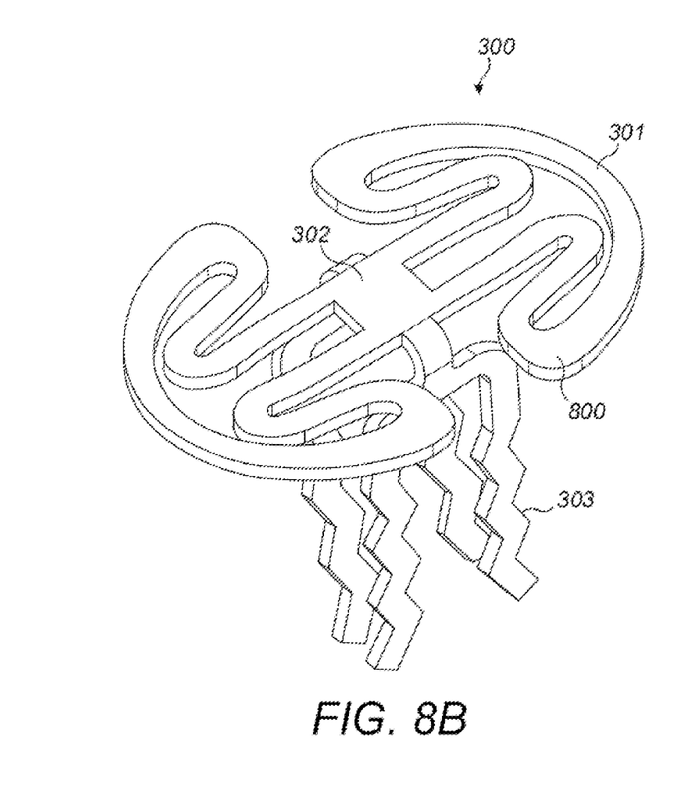

FIGS. 6A-6B show another embodiment of a middle ear prosthesis 300 with deformable wing extensions 600 on the head end 301 adapted for fixation of the head end 301 at the tympanic membrane. FIG. 7 shows a further such embodiment with wing extension end connectors 700 that are adapted to connect opposing ends of the wing extensions 600 by a snap-in mechanism which can be released again. As shown in FIGS. 8A-8B, an embodiment of a MEP 300 where the head end 301 includes extended deformable wings 800 which are bendable extension elements which are bent into final position after bending the extension legs 300.

Although various exemplary embodiments of the invention have been disclosed, various changes and modifications can be made which will achieve some of the advantages of the invention without departing from the true scope of the invention.

What is claimed is:

1. A middle ear prosthesis made of a deformable material and comprising:
   a planar head end with a central portion and a pair of wings extending laterally outward from the central portion, the head end configured to engage with a tympanic membrane of a patient; and
   an opposing pair of U-shaped stapes engagement legs coupled to opposing sides of the central portion and extending downwardly from the central portion, wherein the engagement legs are configured to have an adjustable length for engagement with the stapes in the middle ear of the patient;
   wherein the head end and the engagement legs are configured to transmit vibrations from the tympanic membrane to the stapes for perception as sound by the patient.

2. The prosthesis according to claim 1, wherein the deformable material is made from a thin metal material.

3. The prosthesis according to claim 1, wherein the central portion is thicker than other portions of the prosthesis.

4. The prosthesis according to claim 1, wherein the engagement legs are thinner than other portions of the prosthesis.

5. The prosthesis according to claim 1, wherein the engagement legs have a straight shape.

6. The prosthesis according to claim 1, wherein the engagement legs have a zig-zag shape.

7. The prosthesis according to claim 1, wherein the U-shape of the engagement legs forms an opening, such that a distance between the engagement legs at a portion of the opening is configured to be smaller than the thickness of a portion of the stapes where engaged by the engagement legs.

8. The prosthesis according to claim 1, wherein the U-shape of the engagement legs forms an opening, such that a distance between the engagement legs at a portion of the opening is configured to be larger than the thickness of a portion of the stapes where engaged by the engagement legs.

9. The prosthesis according to claim 1, wherein the engagement legs each include a leg end connectors, such that each leg end connector is positioned at a distal end of each corresponding engagement leg, the leg end connectors are configured to connect corresponding ends of the opposing pair of engagement legs.

10. The prosthesis according to claim 1, wherein the wings include deformable wing extensions configured to fix the head end to the tympanic membrane.

11. The prosthesis according to claim 10, wherein the wing extensions include extension end connectors configured to connect opposing extension ends.

12. A method of forming a middle ear prosthesis comprising:
   providing a planar sheet of deformable material having a central portion connected to an opposing pair of U-shaped stapes engagement legs;
   bending the engagement legs downwardly from the planar sheet towards each other so that the engagement legs are configured to engage with the stapes of a patient; and
   forming a head end from a remaining portion of the planar sheet, the head end including the central portion and a pair of wings extending laterally outward from the central portion, the head end configured to engage with the tympanic membrane of the patient.

13. The method according to claim 12, wherein the deformable material is made from a thin metal material.

14. The method according to claim 12, wherein providing the planar sheet includes using micro-laser cutting to shape the planar sheet.

15. The method according to claim 12, wherein the planar sheet is less than 0.2 mm thick.

16. The method according to claim 12, wherein the planar sheet has a uniform thickness.

17. The method according to claim 12, wherein the planar sheet has a non-uniform thickness.

* * * * *

UNITED STATES PATENT AND TRADEMARK OFFICE
CERTIFICATE OF CORRECTION

Page 1 of 1

PATENT NO. : 10,888,418 B2
APPLICATION NO. : 16/327883
DATED : January 12, 2021
INVENTOR(S) : Steinhardt et al.

It is certified that error appears in the above-identified patent and that said Letters Patent is hereby corrected as shown below:

In the Claims

In Column 6, Line 13:
Replace "connectors"
With --connector--

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*